(12) United States Patent
Thijs et al.

(10) Patent No.: US 6,818,766 B2
(45) Date of Patent: Nov. 16, 2004

(54) PROCESS FOR MAKING BICALUTAMIDE AND INTERMEDIATES THEREOF

(75) Inventors: Lambertus Thijs, Wijchen (NL); Rolf Keltjens, Nÿmegen (NL); Gerrit Jan Bouke Ettema, Nÿmegen (NL)

(73) Assignee: Synthon BV, Nijmegen (NL)

( * ) Notice: Subject to any disclaimer, the term of this patent is extended or adjusted under 35 U.S.C. 154(b) by 0 days.

(21) Appl. No.: 10/261,492

(22) Filed: Oct. 2, 2002

(65) Prior Publication Data

US 2003/0073742 A1 Apr. 17, 2003

(51) Int. Cl.[7] .................... C07D 265/34; C07D 263/04; C07D 317/12; C07C 317/06; C07C 255/03
(52) U.S. Cl. ...................... 544/105; 548/227; 549/296; 558/413; 558/414; 560/11; 562/429
(58) Field of Search ................................ 558/413, 414; 560/11; 562/429; 544/105; 548/227; 549/296

(56) References Cited

U.S. PATENT DOCUMENTS

| 4,636,505 A | 1/1987 | Tucker |
| 5,985,868 A | 11/1999 | Gray |
| 6,019,957 A | 2/2000 | Miller et al. |
| 6,300,514 B1 * | 10/2001 | Takahashi et al. ............ 560/17 |

FOREIGN PATENT DOCUMENTS

| EP | 0100172 | 8/1987 |
| WO | WO0058279 | 10/2000 |
| WO | WO0100608 A1 | 1/2001 |
| WO | WO0128990 A2 | 4/2001 |
| WO | WO0134563 A1 | 5/2001 |
| WO | 02/100339 A2 * | 12/2002 |

OTHER PUBLICATIONS

Gao et al., "Catalytic Asymmetric Epoxidation of Kinetic Resolution: Modified Procedures Including in Situ Derivation": J. Am. Chem. Soc., 1987, pp. 5765–5780.

Tucker et al., "Nonsteroidal Antiandrogens. Synthesis and Structure–Activity Relationships of 3–Substituted Derivatives of 2–Hydroxypropionanilides" : J. Med. Chem., vol. 31, 1988, pp. 954–959.

Shao et al., "A New Asymmetric Synthesis of α–Methyleysteines via Chiral Aziridines": J. Org. Chem. vol. 60, 1995, pp. 790–791.

Zefirov, et al., Journal of Organic Chemistry of the USSR, vol. 22 (2), 1986, pp. 398–399.

Oxley et al. "Amidines. Part II. Preparation of Cyanides, Amides, and Amidines from Carboxylic Acids": Journal of The Chemical Society, 1946, pp. 763–771.

Johnson et al. "Catalytic Asymmetric Dihydroxylation," 1993, pp. 227–273.

Johnson et al. "Catalytic Asymmetric Epoxidation of Allylic Alcohols," 1993, pp. 103–158.

Maryanoff et al., J. Med. Chem., vol. 30, 1987, pp. 880–887.

* cited by examiner

Primary Examiner—Johann Richter
Assistant Examiner—Ebenezer Sackey
(74) Attorney, Agent, or Firm—Mark R. Buscher

(57) ABSTRACT

Bicalutamide and/or its intermediates are made by the use of p-fluorobenzenesulfinic acid salt as a reagent.

8 Claims, No Drawings

PROCESS FOR MAKING BICALUTAMIDE AND INTERMEDIATES THEREOF

BACKGROUND OF THE INVENTION

The present invention relates to a process for making bicalutamide and/or its intermediates using a sulfinic acid salt and to certain intermediate compounds useful in the production of bicalutamide.

Bicalutamide is the common name for the compound 4-cyano-3-trifluoromethyl-N-(3-p-fluorophenylsulfonyl-2-hydroxy-2-methylpropionyl)aniline, and is represented by the formula (1):

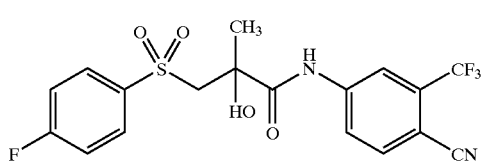

(1)

Bicalutamide is a non-steroidal antiandrogen pharmaceutically active agent that is generally used in the treatment of prostate cancer; i.e., for androgen deprivation treatment, although other androgen dependent conditions may also be treated. Bicalutamide is commercially available in a pharmaceutical composition as a racemate under the brand name CASODEX® (Astra-Zeneca). The R-stereoisomer of bicalutamide has been proposed in U.S. Pat. No. 5,985,868 as being more beneficial than the racemate.

U.S. Pat. No. 4,636,505 teaches a genus of acylanilides including bicalutamide as having antiandrogen activity. Three processes are generically put forth for making the various acylanilides. The first process comprises reacting an acid of the formula $HO_2C-CR^5R^6-A^1-X^1-A^2-R^7$ or a reactive derivative thereof with an aniline compound of a specified formula. The substituents $R^5$ and $R^6$ include hydroxyl and methyl groups; $A^1$ includes methyl, ethyl and ethylidene; $X^1$ includes oxygen, sulfur, sulfinyl, sulfonyl, imino, and methylimino; $A^2$ can be a direct link; and $R^7$ includes substituted phenyl. This process is not exemplified in making bicalutamide in the U.S. Pat. No. 4,636,505. Instead, the examples only show this process for making thio or oxy derivatives wherein $X^1$ is sulfur or oxygen. However, the sulfur is taught to be oxidized to sulfinyl or sulfonyl and thus bicalutamide can be produced with subsequent oxidation by this general reaction according to the following reaction scheme:

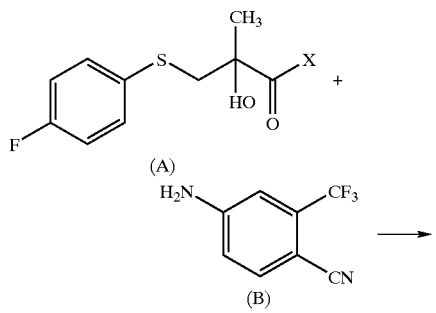

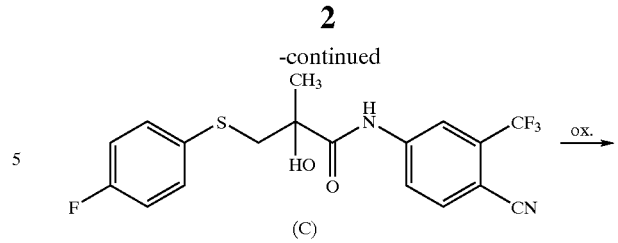

wherein the thio derivative (C) is then oxidized to produce bicalutamide (i.e., sulfur (S) becomes sulfonyl ($SO_2$)). The starting compound (A) having X as a methoxy group was prepared by opening the epoxy-ring of methyl 2,3-epoxy-2-methylpropionate (D) by reacting the same with p-fluorothiophenol (E) as represented below:

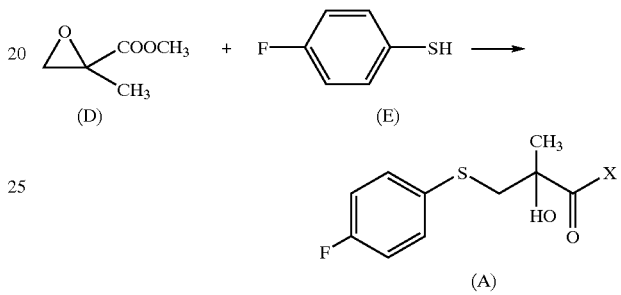

The second process likewise uses a thiophenol compound in order to make a thio analogue of bicalutamide. The process condenses an appropriate thiophenol such as p-fluorothiophenol (E) with an appropriate epoxy-anilide such as (F) to make a thio-analogue of, inter alia, bicalutamide (C). Again, the thio analogue must be oxidized to obtain a sulfonyl linking group in order to make bicalutamide.

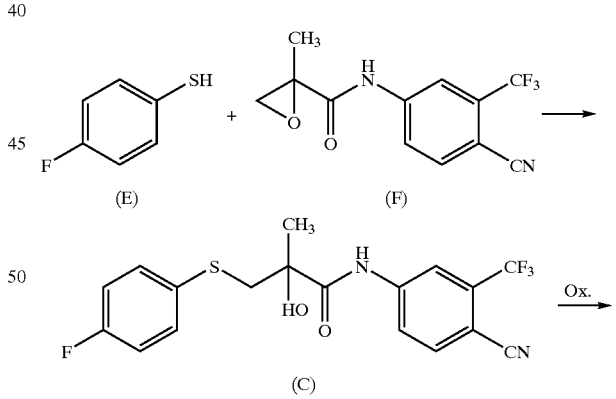

The starting epoxy-anilide (F) was prepared by condensation of the aniline (B) with methacryloylchloride and epoxidation of the so obtained acryl-anilide (G)

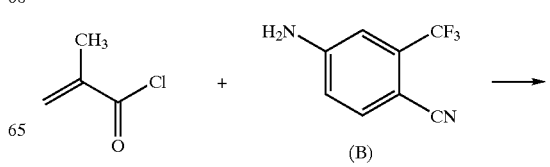

-continued

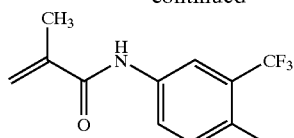

(G)

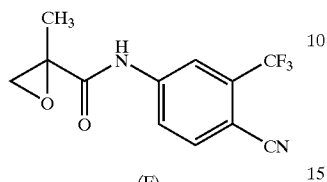

(F)

U.S. Pat. No. 4,636,505 also suggests that the compound (F) may be replaced in this process by an activated hydroxy-compound (H) wherein L is a leaving group:

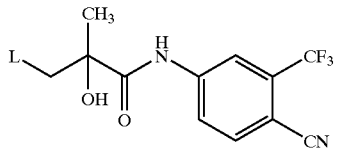

(H)

However, no working example of a process employing a compound of a general formula (H) was provided in the U.S. Pat. No. 4,636,505.

The third process disclosed in U.S. Pat. No. 4,636,505 comprises reacting an organometallic compound of the formula $R^7$—$A^2$—$X^1$—$A^1$—M, where M is a metal radical, with an appropriate aniline derivative such as:

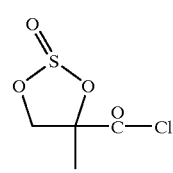

to form the corresponding acylanilide. No example of this process is set forth in the U.S. Pat. No. 4,636,505.

Consistent with the examples, U.S. Pat. No. 4,636,505 teaches that when $X^1$ is desired to be sulfinyl or sulfonyl, the compound may be prepared by oxidizing the corresponding thio-acylanilide compound. Based on these teachings and examples, U.S. Pat. No. 4,636,505 can be seen as teaching the use of a thiophenol of compound (E) above to make bicalutamide by first forming the thio-acylanilide analogue compound (C) followed by oxidation to bicalutamide. The thiophenol can be reacted to form the hydroxy acid of compound (A) which is then subsequently reacted with an aniline compound, or, the thiophenol can be reacted with an acylanilide compound (F) to form the thio bicalutamide analogue.

Other synthetic routes have been proposed for making bicalutamide, especially optically pure bicalutamide. In J. Med. Chem. 885–887 (1988) and J. Med. Chem. 31, 954 (1988) a starting compound of the above compound (H) wherein L is Br in rigid conformation was prepared by bromination of N-methacrylamide of natural (S)-proline (by asymmetric bromolactonisation according to Terashima) to form the cyclic compound (L)

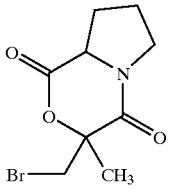

(L)

which was hydrolyzed to yield the (S)-isomer of 2-hydroxy-3-bromoisobutyric acid (N).

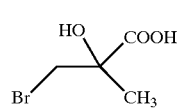

(N)

This was coupled with the aniline (B) to yield the substituted bromohydrine (H) (L=Br) which, after reaction with p-fluorothiophenol (E), provided for thio-bicalutamide (C), however with undesired (S) conformation.

In U.S. Pat. No. 6,019,957, the similar synthesis of (R)-bicalutamide via a iodinated analogue of (H) (i.e. with L=I) was described, starting with (R)-proline. The R-proline provides for the desired conformation. However, it is the unnatural proline isomer and thus highly expensive.

WO01/00608 discloses another route for making racemic or optically pure bicalutamide and also provides a summary of the above processes. In this document, the three routes from U.S. Pat. No. 4,636,505 are set forth for making bicalutamide as FIGS. 1–3. Another route based on the cyclized N-methacrylamide of proline is shown in FIG. 4. The fifth and purportedly inventive route forms a compound (H) where L is —$OSO_2$—R via an amidation reaction of the aniline (B) with a cyclic sulfite-ester of 2,3-dihydroxyisobutyric acid chloride (M)

(M)

The reaction can produce racemic or optically pure bicalutamide depending on the optical purity of the starting 2,3-dihydroxy-2-methyl-propionic acid used to make the cyclic sulfite-ester (M). According to FIG. 5, the compound (H) is reacted with the sodium salt of p-fluorothiophenol to make the thio analogue of bicalutamide (C) followed by oxidation thereof to produce bicalutamide.

WO 01-28990 also describes several methods for how to obtain bicalutamide, optionally via a stereoselective synthesis of the compound (A). The processes include the use of an oxiran ring as in U.S. Pat. No. 4,636,505, a cyclized proline derivative similar to the above articles, or citramalic acid. The later process starts from natural S-citramalic acid which is firstly protected by bromal and brominated upon decarboxylation to form a compound (K).

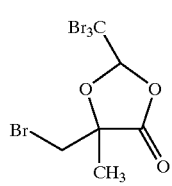

(K)

This compound is condensed with p-fluorothiophenol (E) with subsequent hydrolysis of the protective group, resulting in a compound (A), which is then amidated with the aniline (B) and the formed compound (C) finally oxidized to produce bicalutamide.

The fully elucidated processes for making bicalutamide in the above-mentioned documents all use a p-fluorothiophenol compound, albeit with different reaction partners, to provide a thio linkage which is oxidized in a final step to form the sulfonyl linkage required for bicalutamide. But p-fluorothiophenol is a toxic and unpleasant smelling compound making it somewhat difficult to work with, especially on a large scale.

SUMMARY OF THE INVENTION

The present invention relates to the discovery that a p-fluorobenzenesulfinic acid salt can be successfully used as a reagent in the synthesis of bicalutamide and/or the intermediates therefor. Accordingly, a first aspect of the present invention relates to a process for making bicalutamide, which comprises reacting a compound of formula (2)

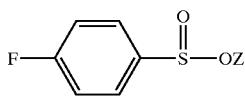

(2)

wherein Z represents a cation, with a suitable reaction partner to form a bicalutamide of formula (1):

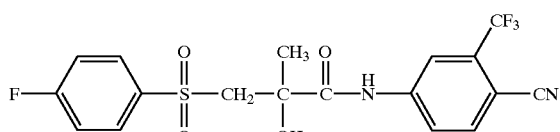

(1)

or a non-bicalutamide product and, if the reacting step produces a non-bicalutamide product, then converting the non-bicalutamide product to a bicalutamide of formula (1). Z is preferably a cation selected from alkali metals, magnesium halides, and ammoniums, and typically is a sodium cation; i.e. sodium p-fluorobenzenesulfinate. The bicalutamide can be obtained in racemic form or enriched by a single optical isomer.

Another aspect of the invention relates to a process, which comprises reacting a compound of formula (2)

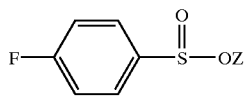

(2)

wherein Z represents a cation; with a compound of formula (3)

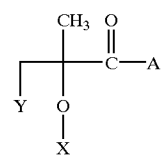

(3)

wherein A represents OR, in which R is a hydrogen, a $C_1$–$C_6$ alkyl, a $C_3$–$C_6$ cycloalkyl, a phenyl, or a benzyl group; or A represents an aniline derivative of the formula:

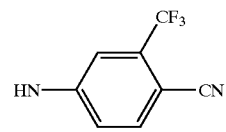

Y represents a leaving group and X represents hydrogen or X and Y join together to form a 3–6-membered heterocyclic ring or X and A join together to form a 5- to 10-membered fused or unfused heterocyclic ring with the proviso that if a ring nitrogen is present, it may be substituted by a 3-trifluoromethyl-4-cyano-phenyl group; to form a compound of the formula (4):

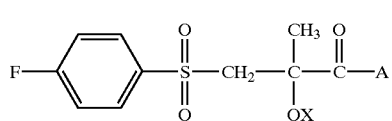

(4)

wherein A and X have the same meaning as in formula (3). When A represents the aniline derivative, the compound of formula (4) is a bicalutamide compound. When A is hydrogen or otherwise represents or is converted to a leaving group, the compound of formula (4) can be reacted with an amine derivative to form a bicalutamide compound of formula (1).

A further aspect of the present invention relates to a compound of the formula (4):

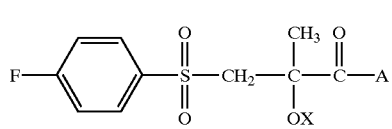

(4)

wherein A represents OR, in which R is a $C_1$–$C_6$ alkyl, a $C_3$–$C_6$ cycloalkyl, a phenyl, or a benzyl group; X represents hydrogen or X and A join together to form a 5- to 10-membered fused or unfused heterocyclic ring with the proviso that if a ring nitrogen is present, it may be substituted by a 3-trifluoromethyl-4-cyano-phenyl group. These intermediates are useful in making bicalutamide.

DETAILED DESCRIPTION OF THE INVENTION

The present invention uses a fluorobenzenesulfinate of formula (2) in making bicalutamide or intermediates thereof.

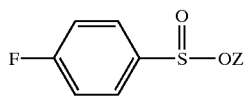

(2)

Z represents a cation and thus is not covalently bonded to the oxygen atom. However, for simplicity, the charges are not shown on the oxygen or cation. Preferably the cation is selected from alkali metals, magnesium halides, and ammoniums. For example, sodium, potassium, magnesium chloride, magnesium bromide, ammonium, dialkylammonium having 1–4 carbon atoms in each alkyl group, are possible cations. Sodium p-fluorobenzenesulfinate, the compound of formula (2) when X is a sodium, is a particularly useful reagent compound in forming bicalutamide or its intermediates.

All of the p-fluorobenzenesulfinic acid compounds of formula (2), and particularly a sodium salt of p-fluorobenzenesulfinic acid, may be prepared by various methods known in the art. One such process is based on a method described by Oxley et al., J. Chem. Soc. 1946, 763 for analogous compounds. The process comprises reaction of p-fluorobenzene sulfonylchloride with sodium sulfite and sodium bicarbonate in a suitable solvent, e.g. in water. Alternatively, p-fluorobenzene sulfonylchloride may be converted to the p-fluorobenzenesulfinic acid by reduction/dehalogenation by sodium borohydride as described in WO 00-58279. Furthermore, a Grignard reagent prepared from p-fluorophenyl bromide and magnesium can be quenched with sulfur dioxide. The resulting bromomagnesium salt of p-fluorobenzenesulfinic acid may be used in crude state or can be converted to the free acid or to an alkali metal salt thereof. The free acid, however formed, can be converted to any of the salt compounds of formula (2).

The p-fluorobenzenesulfinic acid compounds of formula (2) can be used to make bicalutamide, either directly, that is as the last synthetic step, or indirectly, that is by making an intermediate that is subsequently reacted one or more times to form bicalutamide. In this regard, the p-fluorobenzenesulfinates of the present invention can be used instead of the conventional p-fluorothiophenol in any of the above-described reaction schemes; e.g., the three processes generally described in U.S. Pat. No. 4,636,505, the five processes described in the figures of WO01/00608, etc., but is not limited thereto. In short, any reaction scheme that uses the p-fluorobenzenesulfinate of formula (2) in the formation of bicalutamide is included within the present invention. By using the p-fluorobenzenesulfinate of formula (2) to provide the sulfonyl linkage in bicalutamide, and typically the entire p-fluorobenzenesulfonyl terminal group, the usual prior art oxidation of a thio linkage can be avoided. Moreover, the compounds of formula (2) are less toxic, less odiferous and easier to handle than the conventionally used p-thiophenol.

Indeed, it is surprising that a p-fluorobenzenesulfinic acid salt could be used in place of p-fluorothiophenol because of the differences in chemistry. Specifically, an arene sulfinic acid, contrary to a thiophenol, has two reactive centers: the sulfur atom and the oxygen atom. It is apparent that the substitution on the sulfur atom is the desired reaction for purposes of making bicalutamide, however, general knowledge teaches that a sulfinic acid may also undergo substitutions on the oxygen (esterification reactions). Furthermore, thiophenols are also stronger nucleophiles than sulfinic acids. Nonetheless, the reaction can proceed using the p-fluorobenzenesulfinic acid salts of the formula (2). It is preferred that the reaction conditions are adjusted to suppress the O-substitution and/or support the S-substitution and to support nucleophilic substitution. In particular, the preferred environment for reaction of p-fluorobenzenesulfinic acid compound comprises a biphasic reaction system. Such a two-phase system generally comprises water and a water-immiscible solvent, optionally with the aid of a phase-transfer catalyst. Alternatively, the reaction is carried out in a lower alcohol solvent in the presence of a strong acid. The lower alcohol generally has 2 to 6 carbon atoms and is typically ethanol, propanol including isopropanol, butanol or a combination of these. A "strong acid" is an acid that completely dissociates in an aqueous solution such as hydrochloric acid or sulfuric acid, the latter being preferred.

The bicalutamide prepared by the use of a p-fluorobenzenesulfinate of formula (2) is a bicalutamide of formula (1):

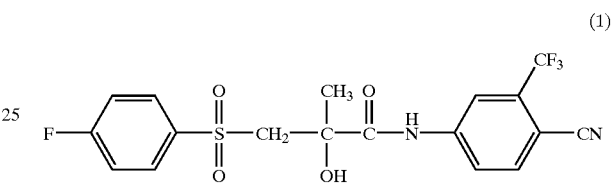

(1)

Because bicalutamide has a chiral carbon it exists in two enantiomeric forms, namely as an R- and S- optical isomer. The bicalutamide of formula (1) can be racemic or an enriched optical isomer including a pure or substantially pure optical isomer. In this context, "enriched" means at least 65% optically pure, more preferably at least 75% optically pure and typically at least 80% optically pure. "Substantially pure" means at least 95% optically pure, preferably at least 99% optically pure. The enriched optical isomer is preferably the (R)-bicalutamide. The enriched optical isomer can be obtained by using optically enriched reaction partners as explained in more detail below, or by separation methods after the formation of a racemic bicalutamide. Suitable separation methods are well known in the prior art and include fractional crystallization techniques and column chromatography among others.

Various reaction partners can be used to form bicalutamide using the p-fluorobenzenesulfinate of formula (2). A preferred reaction partner is a compound of formula (3), which can be represented by the following reaction:

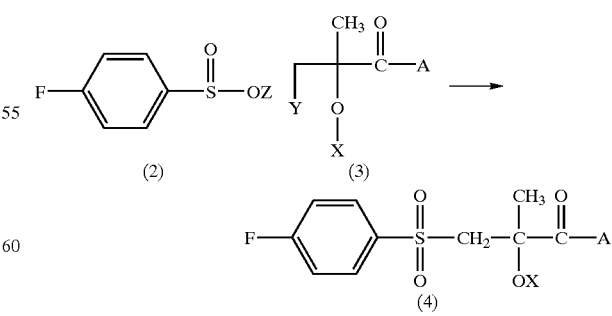

In formula (3), A represents OR, in which R is a hydrogen, a $C_1$–$C_6$ alkyl, a $C_3$–$C_6$ cycloalkyl, a phenyl, or a benzyl group; or A represents an aniline derivative of the formula:

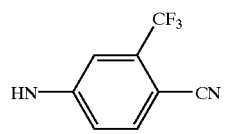

R preferably represents hydrogen, methyl, ethyl, propyl including iso-propyl, butyl including iso- and tert- butyl, or phenyl. Y represents a leaving group and X represents hydrogen. Further the formula can optionally be cyclized such that X and Y join together to form a 3- to 6-membered heterocyclic ring or X and A join together to form a 5- to 10-membered fused or unfused heterocyclic ring. If the ring formed by X and A contains a ring nitrogen, then the ring nitrogen may be substituted by a 3-trifluoromethyl-4-cyano-phenyl group. In formula (4), X and A have the same definitions as in formula (3). In rare circumstances, it is possible that the A group in formula (3) is not the same as the A group in formula (4), albeit both groups are within the definition of A. The same is true for X. For example, if X and A in formula (3) form a ring, it is contemplated that the ring may open during the reaction with the compound of formula (2) thereby making X a hydrogen in the formula (4) compound. However, normally X and A have the same value in both formulae (3) and (4).

Suitable leaving groups for Y are those groups that facilitate nucleophilic substitution by the p-fluorobenzenesulfinate of formula (2), i.e., provide a sufficiently activated reaction partner. Preferred leaving groups are a halogen such as chloro, bromo, or iodo, or a group of the formula —OS(O)$_2$—R$^2$, wherein R$^2$ represents a hydroxyl group, a C$_1$–C$_4$ alkyl group, a phenyl group, or an alkyl-substituted phenyl group. Preferably R$^2$ represents methyl, ethyl, or methyl substituted phenyl. More preferred are iodine, chlorine, bromine, methanesulfonyloxy or toluenesulfonyloxy.

The ring formed by X and Y is a 3- to 6-membered heterocyclic ring. Because the ring is completed by the joining together of X and Y, the ring necessarily contains a ring oxygen bonded to a ring carbon. Further this ring carbon has a methyl substituent. The ring opens upon reaction with the p-fluorobenzenesulfinate of formula (2) to form a compound of formula (4). The ring preferably is comprised of carbons and one or more oxygens, optionally with a ring sulfur atom. Preferred rings are known in the art for synthesizing bicalutamide or related acylanilides using thiophenol compounds; for example, an oxiran ring or a cyclic sulfate ester. Specifically, these rings can be represented as follows:

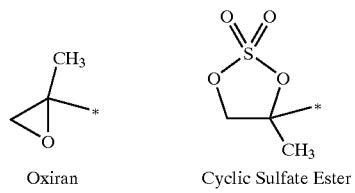

Oxiran     Cyclic Sulfate Ester wherein the * indicates the location of the bond to the carbonyl group of formula (3). The oxiran ring is the most preferred ring formed by Y and X.

In making bicalutamide, the aniline moiety can be present before the reaction with the compound of formula (2), i.e., A is the above-shown aniline derivative, or it can be added afterwards, i.e. A is either the OR group or together with X forms the 5- to 10-membered fused or unfused heterocyclic ring. When A is the aniline derivative, then the compound of formula (4) is a bicalutamide of formula (1). When A is not the aniline derivative, then the compound of formula (4) is further reacted to add the aniline moiety and form bicalutamide. This can be done directly by subjecting the compound of formula (4), especially when A is OH, to an amidation reaction with an amine, preferably an amine of formula (11):

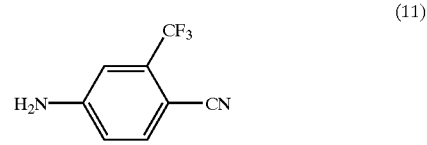

Alternatively, the compound of formula (4) may be converted to a compound of formula (4.1):

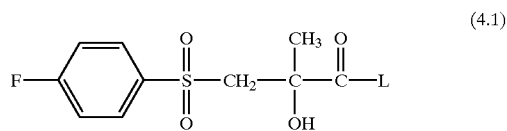

wherein L represents a leaving group for an amidation reaction, and then carrying out the amidation reaction with the above-mentioned amine compound of formula (11) to form a bicalutamide of formula (1). L preferably represents a halogen such as chloro, bromo, or iodo, or a group of the formula —OS(O)$_2$—R$^2$, wherein R$^2$ represents a hydroxyl group, a C$_1$–C$_4$ alkyl group, a phenyl group, or an alkyl-substituted phenyl group. Preferably R$^2$ represents methyl, ethyl, or methyl substituted phenyl. More preferred are iodine, chlorine, bromine, methanesulfonyloxy or toluenesulfonyloxy. In either event, the amidation reaction conditions may generally be similar to those as used for making the thio-analogues of bicalutamide in EP 100172.

If desired and whenever produced in a racemic form, the compounds of formula (4) may be resolved into single enantiomers such as by using methods analogous to those disclosed in WO 01-34563.

The 5- to 10-membered heterocyclic ring formed by A and X is preferably hydrolyzable to form a compound of formula (4) where A is an OR group or a compound of formula (4.1). More preferably the ring provides the methyl and hydroxyl groups in an optically enriched form so that optically enriched bicalutamide can be obtained. Preferred are rings formed by cyclizing proline derivatives or citramalic acid or its derivatives. Specific compounds of formula (3) where A and X have joined together include compounds of formula (3A), (3B), and (3C):

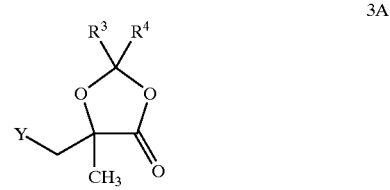

-continued

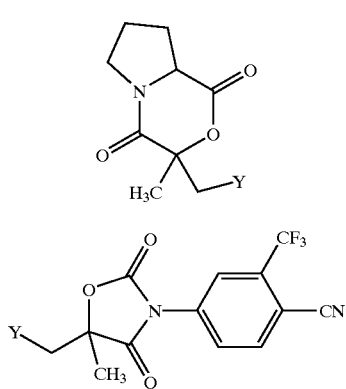

Each of the above compounds can be reacted with p-fluorobenzenesulfinate of formula (2), Y being a leaving group. The resulting compound can be hydrolyzed to open the ring. In the case of formula (3A) and (3B), the ring open compound is either a compound of formula (4.1) or converted to such a compound and then subjected to amidation as described above to form a bicalutamide of formula (1). In the case of formula (3C), hydrolyzing the ring results in a bicalutamide of formula (1) as the aniline moiety is already present.

The compounds of formula (4) where A is the group OR but R does not include hydrogen or A and X form the above-mentioned ring, are useful intermediates and form a particular aspect of the present invention.

The invention will be further described with reference to several compounds and intermediates for the compounds of formula (3) wherein A represents the aniline derivative, (formula (5) series) and several compounds and intermediates for compounds of formula (3) wherein A does not represent the aniline derivative (formula (6) series). The first group of processes uses the compound (2) to provide directly a bicalutamide of formula (1), essentially in one reaction step, as shown in the scheme:

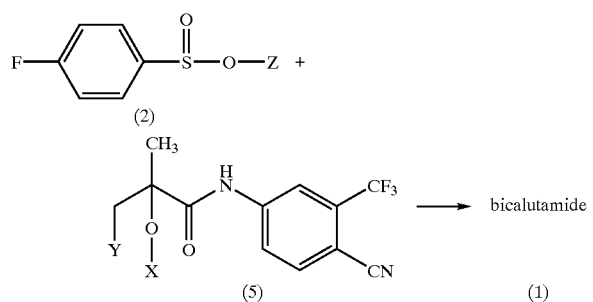

Useful reaction partners of general formula (5) comprise:
1. An Epoxy-amide Compound (5A)

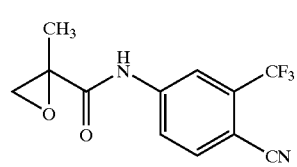

The compound of formula (5A) may be prepared, e.g., by a condensation of 5-amino-2-cyanobenzotrifluoride with methacryloylchloride, followed by epoxidation of the resulting amide (7) as shown below:

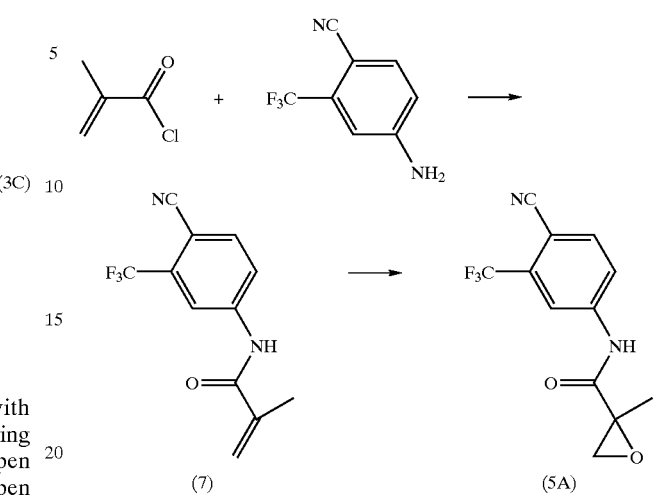

An example of such process is disclosed in EP 100172. The reaction between 5-amino-2-cyanobenzotrifluoride and metacryloylchloride preferably proceeds in a dipolar aprotic solvent, such as N,N-dimethylacetamide. Crude metacroyl amide product (7) may be isolated in solid state and purified by common methods, e.g. by crystallization. The preferred solvent for crystallization is toluene.

The amide (7) may be epoxidated for instance by a peracid, e.g. m-chloroperbenzoic acid, in an inert solvent, or by hydrogen peroxide in a presence of acetic acid anhydride and a catalyst (such as wolframic acid or a heteropoly acid such as phosphomolybdenic acid).

The method, as described, provides the compound (5A) as a racemate. The enantiomerically enriched compound (5A) may be obtained e.g. by an asymmetric epoxidation or by a suitable chemical conversion of a chiral precursor, e.g. by a ring-closure of an enantiomerically enriched hydroxy-compound of formula (5C) discussed hereinafter by an alkali, e.g. potassium carbonate, in a suitable solvent, e.g. in methanol.

2. A Hydroxy-compound of General Formula (5B)

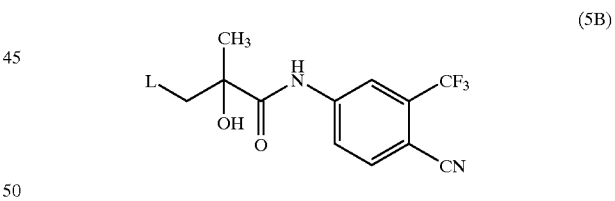

wherein L is a suitable leaving group, for instance a halogen atom, preferably bromine or iodine, or an alkyl- or arylsulfonyloxy group, preferably methane sulfonyloxy group or p-toluenesulfonyloxy group. Preferred compounds for reaction with compound (2) are compounds (5B) wherein L is bromine or iodine.

A compound (5B) wherein L is halogen (a halohydrine), may be produced from the above amide of formula (7) by an addition reaction with a hypohalite, e.g., hypochlorite. Under such conditions, the obtained compound (5B) is a racemate.

This halohydrine however could be prepared also by opening the oxiran ring of the epoxy-compound (5A) by a hydrohalic acid.

The halohydrine (5B, L=bromine) in rigid conformation may be prepared according to a method described in J.Med.Chem.31, 885–887 (1988) or U.S. Pat. No. 6,019,957.

Compounds of formula (5B), wherein L is alkyl- or arylsulfonyloxy group, are less reactive for direct reaction with (2). However, they may be transformed to corresponding bromo- or iodo analogues, e.g. by treatment with an alkali metal halide, e.g. by sodium iodide. Alternatively, they may be transformed into the epoxide compound (5A) by a treatment with a base, e.g. by sodium carbonate.

The compounds (5B) wherein L=RSO$_2$O— group, may prepared by opening the oxiran ring of the epoxy-compound (5A) by a corresponding sulfonic acid R—SO$_2$OH. Alternatively, the compound (5B) wherein L=RSO$_2$O— group, may also be prepared according to WO 01-00608 by an amidation reaction of the amine of formula (11) with a cyclic sulfo-ester of 2,3-dihydroxyisobutyric acid chloride. As a product of workup, a geminal-diol compound (5C)

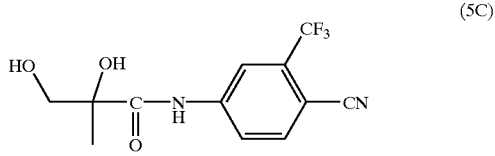

(5C)

is formed and this compound is esterified by a corresponding alkyl- or aryl sulfonyl halide. The above geminal diol-compound (5C) is thus a useful intermediate for making other compounds of general formula (5), both in racemic or in enantiomerically enriched forms.

Apart of the process disclosed above, the compound of the formula (5C) may also be prepared by a dihydroxylation of the amide (7). To prepare the compound (5C) in a racemic form, the amide (7) is treated with a suitable oxidation agent, for instance by N-methylmorpholine-N-oxide (NMO) and osmium tetroxide in a suitable inert solvent. The reaction proceeds at ambient or close to ambient temperatures. Elaboration of the reaction mixture can proceed by conventional methods.

Alternatively, the compound (5C) may be prepared from the amide (7) by a dihydroxylation reaction according to Sharpless. In such a case, the compound (5C) is provided enriched by a single enantiomer. Sharpless dihydroxylation is described, e.g. in Johnson, R. A., Sharpless, K. B., Catalytic Asymmetric Synthesis, Ojima I. ed., Wiley-VCH, New York, 1993. In brief, the reaction employs a chiral oxidizing catalyst comprising either dihydroquinidine 1,4-phthalazinediyl diether (AD-mix-beta) or dihydroquinine 1,4-phthalazinediyl diether (AD mix alpha).

In another alternative, the compound (5C) may be produced by amidation of 2-methyl-2,3-dihydroxypropionic acid esters (compound of formula (6C) shown below). In such a case, the two hydroxy groups in (6C) are advantageously first protected by a suitable protective group, e.g. by means of an acetonide. The protected ester—a compound of formula (8)—

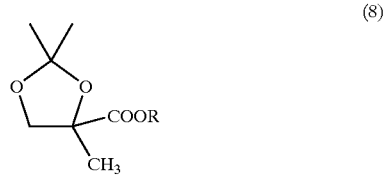

(8)

is first saponified to an acid (R=H) or to a salt, e.g. sodium salt (R=Na) and then amidated with the amine compound of formula (11) under conventional conditions, e.g. in the presence of an activated chloride, e.g. thionylchloride or oxalylchloride, to yield a protected amide (5E).

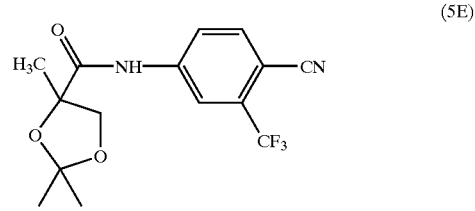

(5E)

The acetonide protective group is then removed under conventional conditions, yielding the desired (5C). As will be shown below, the starting compounds (6C) may be prepared in an enantiomerically enriched form. Accordingly, if such enriched starting material is used for the synthesis of compounds of formula (5C), such compounds are provided also enantiomerically enriched.

The racemic dihydroxy-compound (5C) may be subjected to optical resolution in order to obtain optically enriched reaction partners. Particularly suitable is a method employing optical resolution of a diastereomeric pair of chiral esters of the formula (5F)

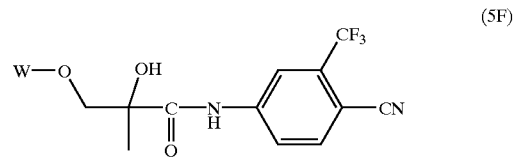

(5F)

wherein W is an acyl moiety derived from an acid having its alpha-carbon chiral. An example of such chiral acid is (−)-camphanic acid. For instance, a mixture of enantiomers of (5C) reacts with (−) camphanic acid chloride and the obtained diastereomeric pair of compounds (5F) (W=(−) camphanoyl) is resolved by a conventional method, e.g. by a column chromatography, to fractions that are enriched by a single diastereomer. Any of the so obtained fractions is subjected to a hydrolysis, preferably alkaline hydrolysis, to remove the camphanoyl group. Thereby, an enantiomerically enriched compound (5C) is obtained.

3. A Cyclic Sulfate Compound (5D)

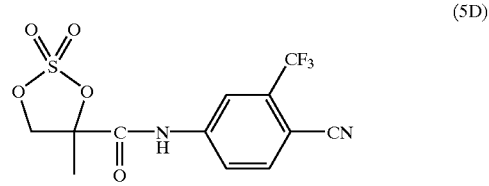

(5D)

Compound of formula (5D) may be prepared by oxidation of an intermediate cyclic sulfite-ester, which in turn may be prepared, e.g. from the geminal diol (5C) by a reaction with thionylchloride and an oxidation agent. The oxidation may be performed, e.g., by ruthenium (III) chloride/sodium periodate. The conversion of (5C) to (5D) may be performed in one process step.

The reaction between the above reactive compounds of the general formula (5), especially (5A), (5B), and (5D), and p-fluorobenzenesulfinic acid salt compound (2), whereby bicalutamide is obtained, preferably proceeds in a bi-phasic system comprising water and a water-immiscible solvent, preferentially in the presence of a phase-transfer catalyst.

The water phase may also comprise a suitable buffer imparting the reaction pH from about 6.5 to about 7.5, e.g. a phosphate buffer. The buffer suppress undesired side reactions on the oxygen. The temperature of contact may be from ambient to reflux, the latter being preferred. The bicalutamide product concentrates in the organic phase and may be isolated therefrom and purified by ordinary methods.

In another variant, the p-fluorobenzenesulfinic acid salt (preferably sodium salt) reacts with the compound (5) in a lower alcohol, e.g. in ethanol. It is an advantage of this solvent that the sulfinate is soluble therein, at least at elevated temperature. A strong, non-nucleophilic acid is recommended to be present in small amounts to form a buffer with the sulfinate. The bicalutamide product crystallizes, together with inorganic salts, from the solvent and may be isolated by filtration. The inorganic salts may be removed by trituration of the solid residue by water.

If the starting compound (5) is used in an enantiomerically enriched form, then the resulting bicalutamide is accordingly enantiomerically enriched. It should be noted that (S) enantiomer of the compound (5) may provide (R)-bicalutamide and vice versa, dependent on the reaction conditions.

A second group of processes reacts p-fluorobenzenesulfinic acid salt of formula (2) with a suitable reaction partner to provide a compound of general formula (4) wherein A is not the aniline derivative. Instead, this compound (4) is used as an intermediate in further reaction to yield bicalutamide, e.g. by contacting it with the appropriate amine, preferably an amine compound of formula (11). If the reactivity of the group A is unsuitable for reaction with the amine, then the compound can be converted to a compound of formula (4.1) where in L is preferably a halogen atom, e.g. chlorine or bromine. The compounds of formula (4) may be produced and further used in a racemic form, or, alternately, as an enriched single optical isomer.

Suitable reaction partners of p-fluorobenzenesulfinates (2) in making compounds of formula (4) are compounds of general formula (6):
wherein A has the same meaning as in the case of compounds of formula (4) other than as the aniline derivative and D is either a leaving group such as halogen, e.g. bromine or iodine, an alkyl- or arylsulfonyloxy group such as methanesulfonyloxy group, or D represents a bond forming an oxirane or cyclic sulfate ring together with the OH— group.

Useful reaction partners of formula (6) comprise:
1. An Epoxy-compound (6A)

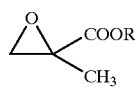

The compound (6A), wherein R=methyl, may be prepared by epoxidation of methyl methacrylate by a hydrogen peroxide, preferably under catalysis with a transition metal compound (e.g. wolframic acid). Alternatively, the epoxidation agent may be an organic peracid, for instance m-chloroperbenzoic acid. In this case, the reaction proceeds by heating in inert solvent, preferably under presence of a radical scavenger to increase the stability of the peracid, for instance bis (3-tert-butyl-4-hydroxy-5-methyl phenyl) sulfide.

In an optically active form, the compound (6A), wherein R=hydrogen, can be prepared also by oxidation of a chiral epoxy-alcohol (9),

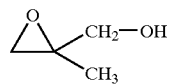

which in turn may be prepared by Sharpless asymmetric epoxidation of corresponding 2-methylallylalcohol (Gao et al. JACS 109, 5765–5780 [1987]). The ruthenium-catalyzed method of oxidation of (9) leading to (6A) has been suggested in J. Org. Chem. 60, 790–791 (1995).

2. A Hydroxy-compound (6B)

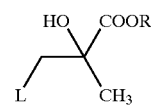

wherein Y is a leaving group such as bromine or iodine atom. The compounds (6B) may be prepared by dihydroxylation of methacrylic acid esters (10)

for instance by NMO/osmium tetroxide or potassium permanganate. The product of dihydroxylation reaction is a compound of formula (6C),

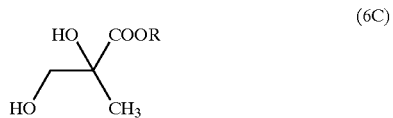

which may be converted into the compounds (6B) by substitution the OH— group by a halide. Depending on the conditions of the dihydroxylation reaction, the compound (6C) may be prepared either as a racemate or enriched by a single enantiomer. For instance, the Sharpless dihydroxylation as discussed above provides the compound (6C) in an enantiomerically enriched form. Accordingly, the desired compound (6B) may be obtained also enantiomerically enriched.

In this consequence, particularly interesting esters of methacrylic acid of the formula (10) are esters with a chiral alcohol, e.g. with L(-)-menthol. Such esters are represented by formula (10), wherein R is a chiral moiety derived from a chiral alcohol. After conventional dihydroxylation of such esters (e.g. by N-methylmorpholine oxide catalyzed by osmium tetroxide), the obtained racemic mixture of chiral dihydroxy esters (6C) may be easily resolved in the single diastereomers by conventional methods, e.g. by preparative column chromatography. Optionally, the menthol-moiety may then be removed by saponification or transesterification. Consequently, an enantiomerically enriched compound of formula (6B) may be obtained as well.

The compound (6B), wherein L is Br or I may be also prepared in enantiomerically pure form by the "proline" method according to J. Med. Chem.885–887 (1988). As discussed above, the disadvantage of this method is that the cheap natural proline provides for the undesired (S) conformation of this compound.

3. A Cyclic Sulfate Ester (6D)

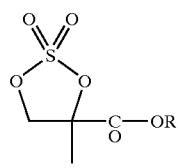

(6D)

The compound of formula (6D) wherein R is an ethyl group may be prepared by a reaction of ethyl 2-methylacrylate with phenyliodine(III)sulfate or oxodiphenyl-diiodine(III)sulfate as described by Zefirov et al. in Zh.Org.Khim. 22(8), 451 (1986).

The processes using any of the above reactive compounds of the general formula (6), especially (6A), (6B), and (6D), react with p-fluorobenzenesulfinic acid compound of the formula (2), particularly with sodium p-fluorobenzenesulfinate, under conditions of nucleophilic substitution. Reaction conditions may be similar as described above for the first general processes. In particular, the both reaction partners react in a bi-phasic system comprising water and a water-immiscible solvent, under presence of a phase-transfer catalyst. The reaction product can be converted by a bicalutamide compound, with or without isolation or modification of the leaving group, by amidation with the amine of formula (11) as explained above.

Apart from the compounds of formula (3), the p-fluorobenzenesulfinic acid salt (2) can be reacted with other suitable reaction partners to yield the desired compounds of formula (4). For instance, one such process starts from a compound of formula (3.1)

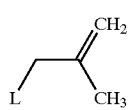

(3.1)

wherein L is a leaving group such as halogen; preferred leaving group is bromine. The 3-bromo-2-methylpropene, i.e. a compound of formula (3.1), wherein L is bromine, is commercially available.

It may react with sodium p-fluorobenzenesulfinate in a suitable inert solvent, e.g. in ethanol, to yield an alkene compound of formula (12). Isolation and purification of the intermediate (12) may be preformed by standard methods, e.g. by column chromatography. In subsequent step, the compound (12) is oxidized by a suitable oxidation agent, e.g. by potassium permanganate in water, to yield a diol (13), which is further oxidized to yield the desired hydroxyacid compound of formula (4), wherein X is OH-group.

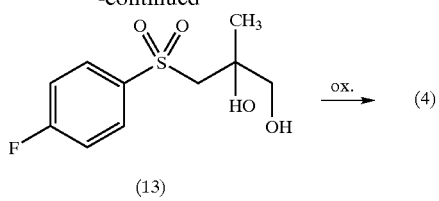

(12)

(13)

The both oxidation reactions may be advantageously performed in one reaction step, i.e. without isolation of the intermediating compound (13), by using the corresponding excess of the oxidation agent.

In another alternative, compound of formula (4) may be also produced by condensation with a compound of formula (3.2).

(3.2)

For example, condensation of bromoacetone, compound 3.2, L=Br, with p-fluorobenzenesulfinic acid salt, cyanolysis of the resulting thiol-ketone (15) and hydrolysis of the resulted cyanhydrin (16) produces a compound of formula (4).

(15)

(16)

Compounds of formula (4) are converted to bicalutamide by an amidation reaction with the amine compound of formula (11) as described above. If desired and whenever produced in a racemic form, the compounds of formula (4) may be resolved into single enantiomers. An example is given in WO 01-34563.

In any of the above procedures, the amine compound of formula (11) may be replaced by an isocyanate compound of formula (17) in order to form the aniline derivative. For instance, the isocyanate (17) may react with the compound of formula (6) according to the following scheme:

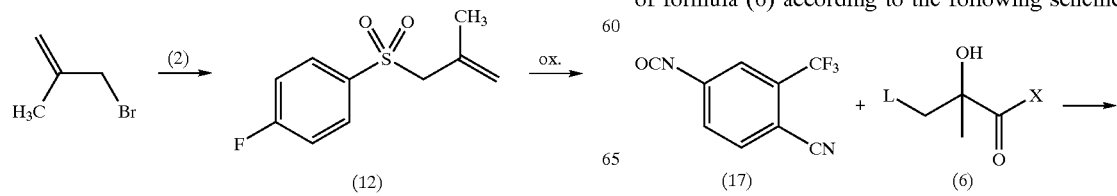

(17)        (6)

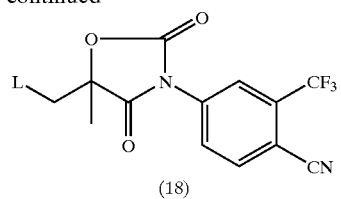

(18)

After condensation of (18) with p-fluorobenzenesulfinate (2), the intermediating cyclic product (19)

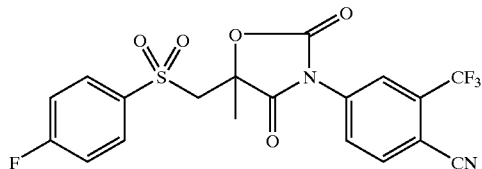

is hydrolyzed, preferably in alkaline medium, to yield bicalutamide. This process can also be carried out to give bicalutamide enriched by a single enantiomer, when starting from optically active (6).

Similarly, the compound (19) may be provided by reacting the isothiocyanate (17) with a compound of formula (4).

Another reaction partner separate from the preferred compounds of formula (3) is one that converts the p-fluorobenzenesulfinate (2) into a compound of formula (20)

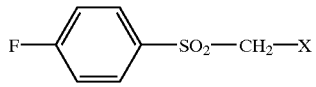

(20)

wherein X is a leaving group such as halogen atom. This compound may be contacted with a suitable reaction partner, for instance with compound (21):

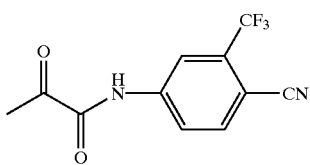

to yield bicalutamide of formula (1). The compound (20) may be prepared by reaction of sodium p-fluorobenzenesulfinate with dichloroacetic acid. The compound (21) may be prepared according to EP 100172.

The invention will be further described with reference to the following non-limiting examples.

EXAMPLE 1

N-[4-cyano-3-(trifluoromethyl)phenyl]-2-methylacrylamide (7)

A 2 liter three-neck flask is charged with 235 g of 4-cyano-trifluoromethylaniline and 671.5 ml of N,N-dimethylacetamide. The solution is cooled to 15° C. and 126 ml of methacroyl chloride is added dropwise under stirring and cooling below 25° C. The mixture is then stirred for 1 hour at room temperature. Reaction mixture is diluted with 20 ml of distilled water and poured into 2678 ml of cooled distilled water. The mixture is then stirred at 5–10° C. for 2 hours. Precipitated solid is filtered and washed with 1500 ml of water. Wet product is suspended in 1020 ml of toluene and heated to reflux. The obtained solution is cooled to 10–20° C. and the resulted suspension is stirred at this temperature for 1 hour. The solid is filtered off, washed by toluene (100 ml) and dried.

Yield: 289 g.

EXAMPLE 2

N-[4-cyano-3-(trifluoromethyl)phenyl]-2-methyl-2-oxiranecarboxamide (5A)

460 mg of the amide (7) from the Example 1 was dissolved in 30 ml of dichloromethane. 560 mg of m-chloroperbenzoic acid (purity 70–75%) was added. The reaction mixture was stirred overnight at reflux. The reaction was monitored with HPLC. The reaction mixture was washed successively with 2×20 ml of a sodium sulfite solution, 2×20 ml of saturated aqueous $NaHCO_3$ and 20 ml of brine. The organic layer was dried ($Na_2SO_4$), filtrated and evaporated under reduced pressure yielding the epoxide (5A) as yellow solid material. Isolated yield: 400 mg (82%). $^1$H- and $^{13}$C-NMR confirmed the expected structure. HPLC: 96% purity.

EXAMPLE 3

N-[4-cyano-3-(trifluoromethyl)phenyl]-2-methyl-2-oxiranecarbox-amide (5A)

10 ml of 30% aqueous hydrogen peroxide is heated to 35–40° C. 20 ml of acetic anhydride is added dropwise under cooling, so that the temperature does not exceed 40–50° C. 0.02 g of wolframic acid is added and the reaction mixture is stirred for 0.5 hours at 50–55° C. 3 grams of the amide (7) is added to the mixture portionwise and the reaction mixture is stirred for 6 hours at 50–55° C. The suspension is then cooled to 20–25° C. and poured, under stirring, into 100 ml of cold (0–5° C.) water. The suspension is stirred for 30 minutes and the solid is filtered off, washed by water and dried at 40–50° C.

Yield: 2.44 g (76.5%).

EXAMPLE 4

Enantiomerically Enriched Methyl 2,3-dihydroxy-2-methylpropanoate (6C)

Step 1: (1R,2S,5R)-2-isopropyl-5-methylcyclohexyl 2-methylacrylate (10, R=menthyl)

Reaction Scheme

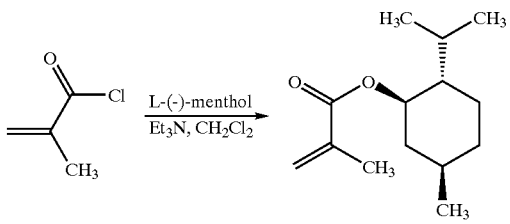

In a 100 ml flask, equipped with a magnetic stirrer, 5.0 g of L-(−)-menthol and 3.51 g of methacryloyl chloride were added to a solution of 6.67 ml of triethylamine in 30 ml of dichloromethane at room temperature. The clear solution turned turbid after a few minutes (exothermic reaction). After 4 hours, the suspension was extracted with 25 ml of 0.5 N HCl, 25 ml of water, 25 ml of saturated aqueous $NaHCO_3$ and 25 ml of brine to give a clear orange solution (after drying over $Na_2SO_4$). Concentrating at reduced pressure gave a light brown/orange oil, which was stored overnight at 4° C. Purification by column chromatography (eluens: ethyl acetate/heptane=1/4) gave 5.30 g (73.8%) of a colourless oil. $^1$H-NMR confirmed the expected structure.

Step 2: (1R,2S,5R)-2-isopropyl-5-methylcyclohexyl-2,3-dihydroxy-2-methyl-propanoate (6C, R=menthyl)
Reaction Scheme

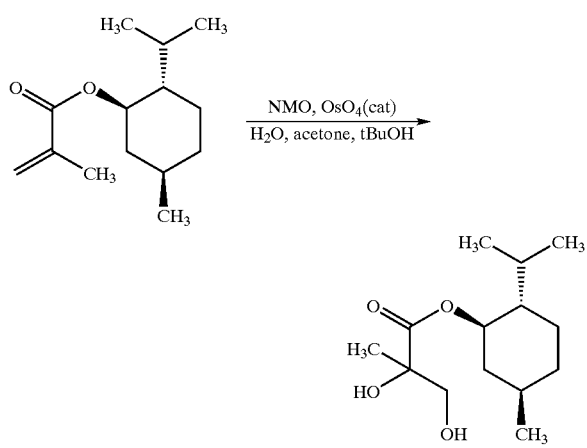

Into a 250 ml flask, equipped with a magnetic stirrer and containing a mixture of 6.02 g of N-methylmorpholine oxide monohydrate and 220 mg of osmium tetroxide in 300 ml of acetone/water (2/5) mixture at room temperature, was added 10.0 g of the menthol ester of Step 1 in 36 ml of tert-butyl alcohol. The reaction mixture was stirred at room temperature overnight. Then a slurry of 10.0 g of NaHSO$_3$ and 10.0 g of Celite in 400 ml of water was added and the resulting mixture was filtered. The filtrate was neutralised with 1N aqueous H$_2$SO$_4$ and the acetone was removed at reduced pressure. Then the pH was set at 2.0 using 1N aqueous H$_2$SO$_4$. The water phase was extracted with 3×350 ml of ethyl acetate. The combined organic layers were dried (Na$_2$SO$_4$) and concentrated at reduced pressure to give the crude diol. Purification by column chromatography (eluens: ethyl acetate/heptane=1/4) gave 10.2 g (89%) of crude product, which was purified by column chromatography (Merck 60 SiO$_2$; eluens=heptane/ethyl acetate=4/1). Result: 2.4 g of slow-moving diastereomer (d.e.=92.3%), 1.9 g of fast-moving diastereomer (d.e.>90%), and a mix-fraction.

Step 3: Decomposition of the menthol derivative (6C, R=menthyl)

The decomposition of any of the diastereomers of the Step 2 was performed according to a process of example 20.

EXAMPLE 5

Enantiomerically Enriched Sodium 2,2,4-trimethyl-1,3-dioxolane-4-carboxylate (8, R=Na)

Step 1: (1R,2S,5R)-2-isopropyl-5-methylcyclohexyl 2,2,4-trimethyl-1,3-dioxolane-4-carboxylate (8, R=menthyl)
Reaction Scheme

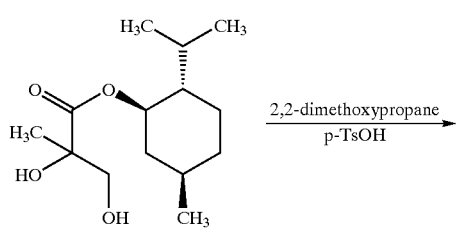

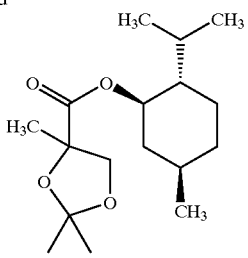

In a 250 ml flask, equipped with a magnetic stirrer, 1.8 g of the diol (6C, R=menthyl) from the Step 2 of Example 4 (fast moving diastereomer) was dissolved in 50 ml of 2,2-dimethoxypropane at room temperature. Then, 100 mg of paratoluenesulfonic acid monohydrate was added, and the resulting mixture was stirred at room temperature for 18 hours. Then, 100 ml of ethyl acetate and 100 ml of saturated aqueous NaHCO$_3$ were added. The aqueous phase was extracted with 100 ml of ethyl acetate. The combined organic layers were washed with 100 ml of brine, dried (Na$_2$SO$_4$) and concentrated at reduced pressure. The crude product was purified by column chromatography (Merck60 SiO$_2$; eluens=ethyl acetate/heptane=1/4) to give the acetonide (8, R=menthyl) (1.855 g; 92%) as a colourless oil. $^1$H-NMR and $^{13}$C-NMR confirmed the structure Step 2: Saponification of the Compound (8, R=menthyl)
Reaction Scheme

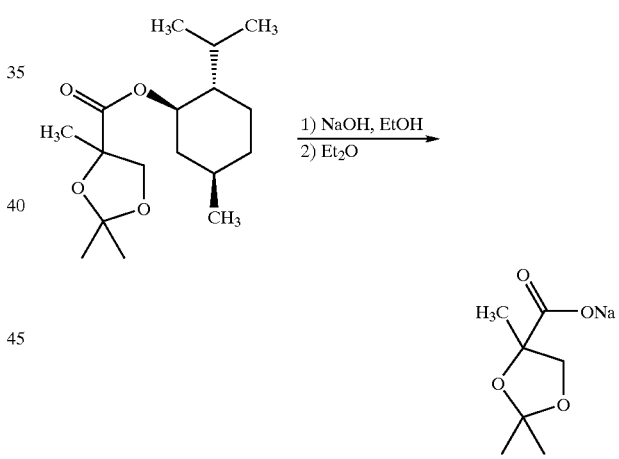

In a 50 ml flask, equipped with a magnetic stirrer, 0.3 g of the menthyl ester (8, R=menthyl) was dissolved in 1 ml of ethanol. At room temperature, 42.2 mg of sodium hydroxide dissolved in 2 ml of ethanol was added. The reaction was monitored by TLC analysis (eluens: ethyl acetate/heptane=1/4). After 4 hours (~15% conversion), more sodium hydroxide was added (total amount ~50 mg), and the reaction mixture was stirred overnight at room temperature. A white solid had formed. Conversion was more than 95%. The reaction was worked-up by addition of 5 ml of diethyl ether. The resulting suspension was stirred for 30 minutes. The white solid was isolated by filtration, washed with 5 ml of diethyl ether and dried overnight at reduced pressure at 40° C. Isolated yield: 0.165 g (90%) of the title sodium salt (8, R=Na). $^1$H-NMR confirmed the structure.

EXAMPLE 6

N-[4-cyano-3-(trifluoromethyl)phenyl]-2,3-dihydroxy-2-methylpropanamide (5C)

Step 1: N-[4-cyano-3-(trifluoromethyl)phenyl]-2,2,4-trimethyl-1,3-dioxolane-4-carboxamide (5E)

Reaction Scheme

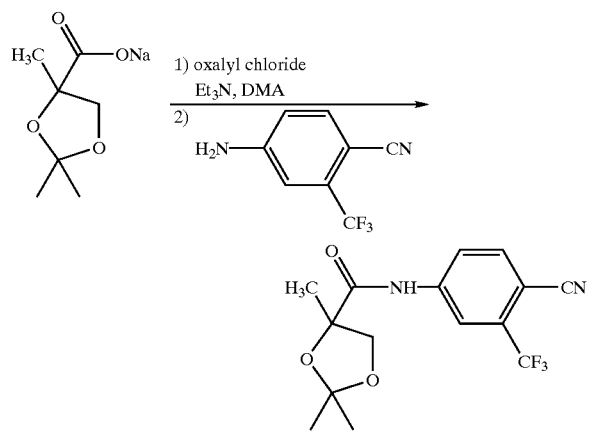

In a 50 ml 3-necked flask, equipped with a magnetic stirrer, under nitrogen at −20° C., 0.3 ml of oxalyl chloride in 1 ml of tetrahydrofuran was added slowly to 0.364 g of the sodium salt of the Example 5 (compound (8), R=Na) in a mixture of 0.5 ml of triethyl amine in 5 ml of dimethylacetamide. The resulting mixture was stirred for 30 minutes at −10° C. Then, a solution of 0.372 g of 4-cyano-3-trifluoromethylaniline in 2 ml of dimethylacetamide was added dropwise and slowly. The conversion was followed by TLC analysis (eluens: ethyl acetate/heptane=2/3). After ~1 hour at room temperature, the reaction mixture was poured into 200 ml of saturated aqueous NaHCO$_3$ solution, and was subsequently extracted with 2×30 ml of ethyl acetate. The combined organic layers were washed with 50 ml of brine, dried (Na$_2$SO$_4$) and concentrated at reduced pressure to give a dark-brown oil, which was purified by column chromatography (Merck 60 SiO$_2$, eluens ethyl acetate/heptane=2/3). Isolated yield: 0.336 g light brown clear oil (51%). $^1$H-NMR confirmed the structure.

Step 2 Deprotection

Reaction Scheme

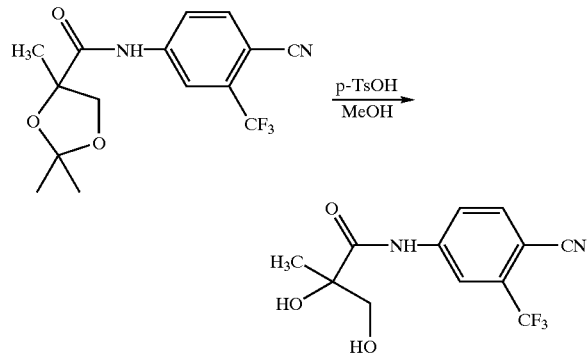

In a 50 ml flask, equipped with a magnetic stirrer, 0.336 g of the acetonide from the Step 1 was dissolved in 10 ml of methanol. Then, 50 mg of paratoluenesulfonic acid monohydrate was added and the resulting reaction mixture was stirred at room temperature for 18 hours. The conversion (TLC: eluens=ethyl acetate/heptane=3/2) was >95%. Then, 50 ml of saturated aqueous NaHCO$_3$ solution was added, and the mixture was extracted with 2×20 ml of ethyl acetate, followed by washing the organic layers with 20 ml of brine, drying (Na$_2$SO$_4$) and concentrating at reduced pressure to give the crude product. Purification by column chromatography (Merck 60 SiO$_2$, eluens ethyl acetate), gave the diol as a slightly yellow oil. Isolated yield: 0.244 g (89%). $^1$H-NMR confirmed the structure.

EXAMPLE 7

N-[4-cyano-3-(trifluoromethyl)phenyl]-2,3-dihydroxy-2-methylpropanamide (5C) Enriched by (2R) Enantiomer Reaction Scheme

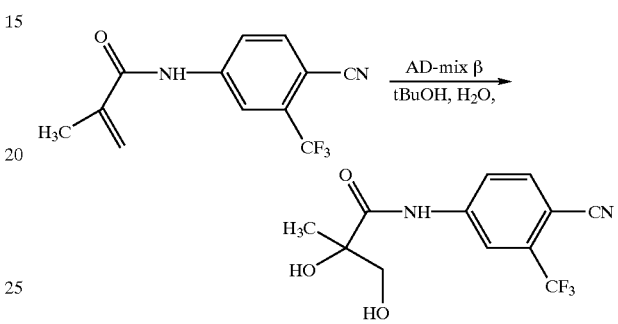

In a 50 ml flask, equipped with a magnetic stirrer, 1.4 g of Sharpless AD-mix β was dissolved in 5 ml of tert-butyl alcohol and 5 ml of water. The mixture was cooled to 0° C., and 0.145 g of the compound (7) was added in one portion. The heterogeneous mixture was stirred vigorously and was allowed to warm to 4° C. over the weekend. The conversion was followed by HPLC and after 7 days, the reaction was worked-up (about 50% conversion of starting material). The reaction was quenched by addition of 1.5 g of Na$_2$SO$_3$. After stirring for 15 minutes, 20 ml of ethyl acetate and 20 ml of water were added. The aqueous layer was extracted with 2×20 ml of ethyl acetate. The combined organic layers were washed with 20 ml of brine, dried (Na$_2$SO$_4$) and concentrated in vacuo. The crude product was purified by column chromatography (Merck 60 SiO$_2$, eluens ethyl acetate) to give ~20 mg of the pure title compound. The enantiomeric excess was determined on a chiral column (HPLC): ~22% e.e.

EXAMPLE 8

N-[4-cyano-3-(trifluoromethyl)phenyl]-2,3-dihydroxy-2-methylpropanamide (5C)

Reaction Scheme

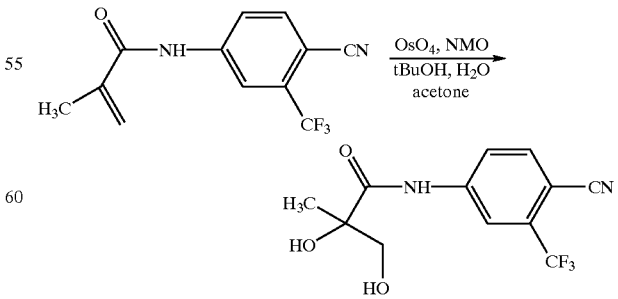

In a 50 ml flask, equipped with a magnetic stirrer, 0.50 g of the compound (7) in 1.8 ml of tert-butyl alcohol was added to a mixture of 0.301 g of N-methylmorpholine-N-oxide (=NMO) (monohydrate) and 16 mg of osmium tetroxide in 15 ml of a water/acetone mixture (5:2). The reaction mixture was stirred at room temperature overnight. The conversion was ~60%. Another 0.30 g of NMO (monohydrate) and 16 mg of osmium tetroxide were added and the reaction was followed with HPLC. Stirring was continued for 3.5 hours. The reaction was worked-up by addition of a slurry of 1.0 g NaHSO$_3$ and 1.0 g of Celite in 40 ml of water. The Celite was removed by filtration, and the filtrate was neutralised to pH 7.0 with 1N aqueous H$_2$SO$_4$, and the acetone was removed at reduced pressure. The remaining solution was set to pH 2.0 with 1N aqueous H$_2$SO$_4$ and was extracted with 3×35 ml of ethyl acetate. The combined organic layers were washed with 35 ml of brine, dried (Na$_2$SO$_4$) and concentrated at reduced pressure. The crude product was purified by column chromatography (Merck 60 SiO$_2$, eluens ethyl acetate) to give the purified (5C) as a slightly coloured oil, which solidified (off-white solid) after a few days. Isolated yield: 0.400 gram (70.5%). $^1$H-NMR confirmed the structure.

EXAMPLE 9

3-[4-cyano-3-(trifluoromethyl)anilino]-2-hydroxy-2-methyl-3-oxopropyl Methanesulfonate (5B, L=methanesulfonyloxy)

Reaction Scheme

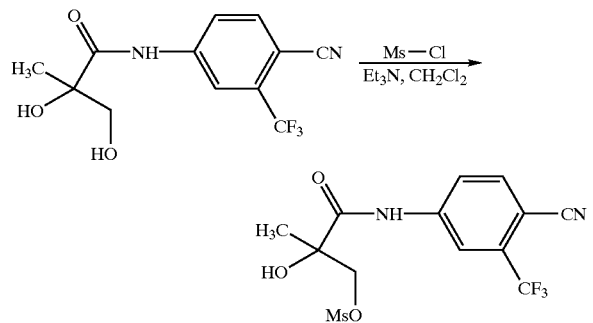

In a 50 ml flask, equipped with a magnetic stirrer, 0.1 ml of triethyl amine was added at 0° C. to a solution of 0.144 g of the diol compound (5C) in 5 ml of dichloromethane. Then, 63 mg of methanesulfonyl chloride was added dropwise. The resulting mixture was stirred and allowed to warm to room temperature. After completion (30 minutes), 20 ml of ethyl acetate and 20 ml of 0.5 N aqueous HCl were added. The organic layer was subsequently washed with 20 ml of water and 20 ml of saturated aqueous NaHCO$_3$. After drying (Na$_2$SO$_4$) and concentrating at reduced pressure, the crude product was purified by column chromatography (Merck 60 SiO$_2$, eluens=ethyl acetate) to give 0.115 g (63%) of the title mesylate compound. $^1$H-NMR confirmed the structure.

EXAMPLE 10

N-[4-cyano-3-(trifluoromethyl)phenyl]-2-hydroxy-3-iodo-2-methylpropanamide (5B, L=I)

Reaction Scheme

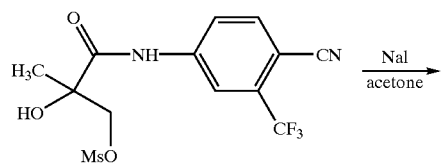

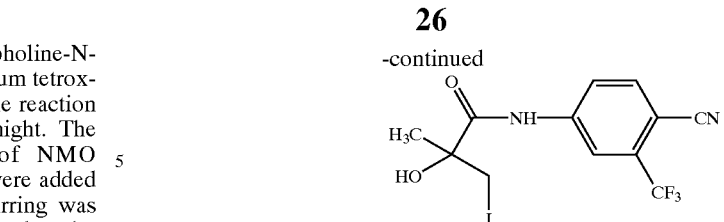

In a 50 ml flask, equipped with a magnetic stirrer, 0.115 g of the mesylate of Example 9 was dissolved in 5 ml of acetone. Then, 0.47 g of sodium iodide was added and the reaction mixture was heated at reflux. The conversion was checked by HPLC. The reaction appeared to be very slow. Therefore, another 1.0 g of sodium iodide and 2 ml of acetonitrile were added. The reaction took 3 days. After addition of 20 ml of ethyl acetate, the reaction mixture was washed with 20 ml of water, 0.5M aqueous Na$_2$S$_2$O$_3$, and brine, dried (Na$_2$SO$_4$) and concentrated at reduced pressure. The crude product was purified by column chromatography (Merck 60 SiO$_2$, eluens=ethyl acetate/heptane=3/2) to give 0.083 g (66%) of the expected iodide (compound 5B, L=I). $^1$H-NMR confirmed the structure.

EXAMPLE 11

3-bromo-N-[4-cyano-3-(trifluoromethyl)phenyl]-2-hydroxy-2-methylpropanamide (5B, L=Br)

Reaction Scheme

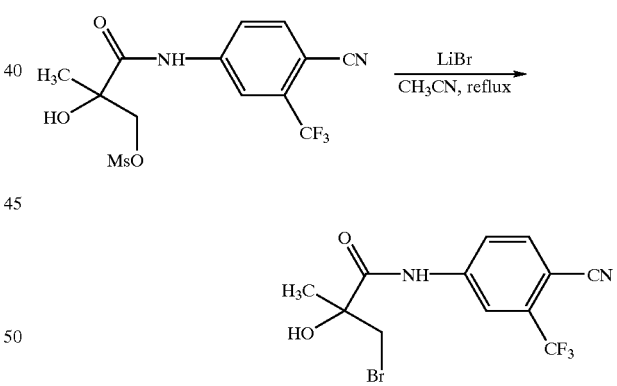

In a 25 ml flask, equipped with a magnetic stirrer, 0.412 g of the mesylate of Example 9 and 0.98 g of lithium bromide were dissolved and heated at reflux in 5 ml of acetonitrile for 3 days. The conversion was followed by HPLC. After a conversion of 90%, the reaction mixture was worked-up. After addition of 20 ml of water, the aqueous phase was extracted with 2×20 ml of ethyl acetate. The combined organic layers were washed with brine, dried (Na$_2$SO$_4$) and concentrated at reduced pressure. Purification by column chromatography (Merck60 SiO$_2$; eluens=ethyl acetate/heptane=1/1) gave 0.184 g of the title bromo-compound. $^1$H-NMR confirmed the structure.

EXAMPLE 12

3-[4-cyano-3-(trifluoromethyl)anilino]-2-hydroxy-2-methyl-3-oxopropyl-4-methylbenzene sulfonate (5B, L=p-toluenesulfonyloxy)

Reaction Scheme

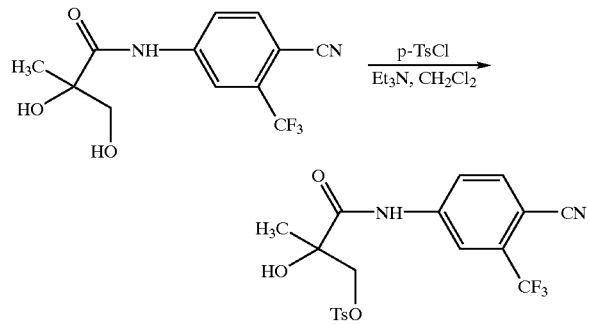

In a 50 ml flask, equipped with a magnetic stirrer, 0.240 g of the diol compound (5C) was dissolved in 5 ml of dichloromethane and was treated with 0.510 g of paratoluenesulfonyl chloride and 0.38 ml of triethyl amine at 0° C. Immediately after addition, the ice-bath was removed and the temperature was allowed to warm to room temperature. The conversion was checked by TLC analysis (eluens=ethyl acetate; starting material) and (eluens=ethyl acetate/heptane=1/1; product). Work-up was performed by addition of 25 ml of ethyl acetate. The organic layer was washed with 20 ml of 0.5N aqueous HCl, 20 ml of water, 20 ml of saturated aqueous NaHCO$_3$, dried (Na$_2$SO$_4$), and concentrated at reduced pressure. Purification by column chromatography (Merck 60 SiO$_2$, eluens ethyl acetate/heptane=1:1), gave two fractions. The second fraction was the product as was determined by $^1$H-NMR spectroscopy. Isolated yield: 0.179 g (45%).

EXAMPLE 13

N-[4-cyano-3-(trifluoromethyl)phenyl]-2-hydroxy-3-iodo-2-methylpropanamide (5B, L=I)

Reaction Scheme

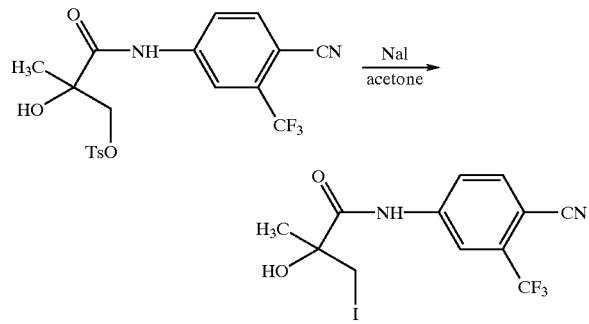

In a 50 ml flask, equipped with a magnetic stirrer, 0.135 g of the tosylate compound of Example 12 was treated with an excess of sodium iodide (>10 equivalents) in 10 ml of acetone at reflux for 48 hours. After cooling to room temperature, the reaction mixture was transferred to a separation funnel and 20 ml of ethyl acetate was added. The organic layer was washed with 20 ml of water, 20 ml of 0.5M aqueous Na$_2$S$_2$O$_3$, and 20 ml of brine, dried (Na$_2$SO$_4$) and concentrated at reduced pressure. The crude product was purified by column chromatography (Merck 60 SiO$_2$, eluens=ethyl acetate/heptane=3/2) to give two fractions. The first fraction was the product as was determined by $^1$H-NMR spectroscopy. Isolated yield: 0.048 g (40%).

EXAMPLE 14

Bicalutamide by Coupling of the Epoxyamide (5A) and Sodium-p-fluorobenzenesulfinate 0.500 g of the epoxyamide (5A) was dissolved in a mixture of 40 ml of chloroform and 40 ml of water and 371 mg of sodium p-fluorobenzenesulfinate was added. Subsequently, 298 mg of tetrabutylammonium bromide was added. The reaction mixture was heated till reflux, while stirring vigorously. The reaction was monitored with HPLC. After 96 hours of reflux, the reaction mixture was cooled to room temperature. 20 ml of chloroform was added and the organic layer was washed with 3×50 ml of water, dried (Na$_2$SO$_4$) and evaporated to dryness. Yield: 860 mg. Purification of the crude product by column chromatography (Merck silica gel 60; eluent: heptane/ethyl acetate=1/1) afforded bicalutamide as white solid. Isolated yield: 380 mg (48%). $^1$H-NMR: confirmed the structure.

EXAMPLE 15

Bicalutamide by Coupling of the Epoxyamide (5A) and Sodium-p-fluorobenzenesulfinate A three necked 500 ml flask was charged with 100 ml of cold ethanol and 1.89 g of 96% sulfuric acid was carefully added under stirring. Then, 14.85 g of sodium p-fluorobenzenesulfinate and 10.0 g of the epoxyamide (5A) was added, the mixture was heated under reflux for 6 hours and evaporated to dryness. The solid residue was mixed with 30 ml of fresh ethanol and stirred for 30 minutes. The solid was filtered and washed with 20 ml of ethanol. The wet cake was transferred into a flask, mixed with 50 ml of hot water (60° C.) and stirred for 30 minutes without heating. The solid was filtered off and washed with 3×20 ml of water. The product was dried at 80° C. Yield: 6.79 g of bicalutamide.

EXAMPLE 16

Bicalutamide by Coupling of the Iodo-compound (5B, L=I) and Sodium-p-fluorobenzenesulfinate Reaction Scheme

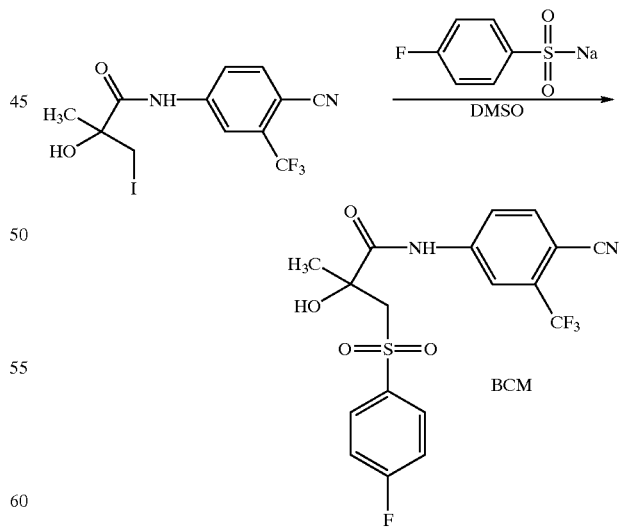

In a 25 ml flask, equipped with a magnetic stirrer, 0.200 g of the iodo-compound (5B, L=I) and 0.200 g sodium p-fluorobenzenesulfinate were dissolved in 3–4 ml of dimethylsulfoxide and heated at 60° C. for 18 hours. During the reaction, next three portions of 0.200 g of sodium p-fluorobenzenesulfinate were added. The reaction was followed with HPLC analysis. To the reaction mixture there was added 30 ml of ethyl acetate, 30 ml of brine and 20 ml of water. The organic layer was washed with 20 ml of 0.5N aqueous HCl, 20 ml of water, and 20 ml of saturated aqueous NaHCO$_3$. After drying (Na$_2$SO$_4$) and concentration in vacuo, the crude product was purified by column chromatography (Merck60 SiO$_2$; eluens=ethyl acetate/heptane=3/2) to give bicalutamide. Isolated yield: 0.050 g (23%).

EXAMPLE 17

(2S)-N-[4-cyano-3-(trifluoromethyl)phenyl]-2-methyl-2-oxirane Carboxamide (5A)

Reaction Scheme

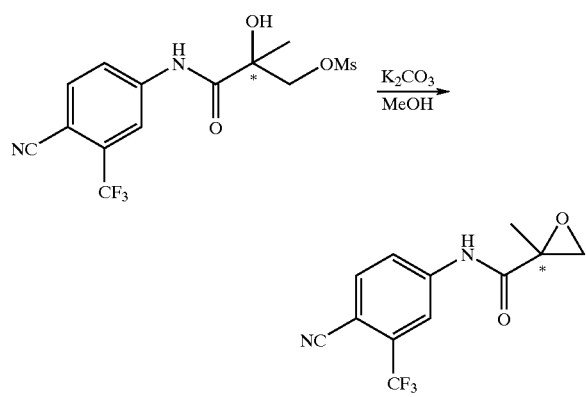

150 mg of the chiral mesylate of Example 23, was dissolved in 15 ml of methanol. 50 mg of potassium carbonate was added. After 1 hour at room temperature, the reaction was completed according to HPLC. 20 ml of diethyl ether and 20 ml of water were added. The organic phase was washed with 3×20 ml of water, dried (Na$_2$SO$_4$), filtrated and evaporated to dryness. Yield: 108 mg (98%), yellow crystals. $^1$H- and $^{13}$C-NMR confirmed the structure. HPLC: 95% purity. HPLC (chiral column): 96.3% e.e.

EXAMPLE 17A

Coupling of Chiral Epoxyamide (5A) and Sodium-p-fluorobenzenesulfinate Resulting in Optically Active Bicalutamide Reaction Scheme

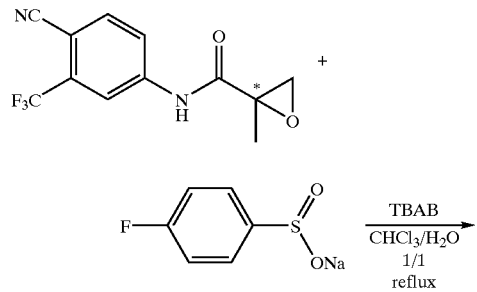

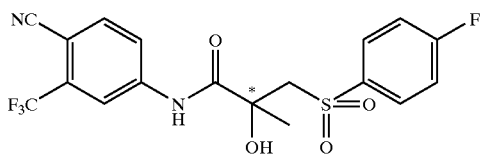

180 mg of the chiral epoxide of example 17 was dissolved in a mixture of 12 ml chloroform and 12 ml of water. 133 mg of sodium-p-fluorobenzenesulfinate and 107 mg of tetrabutylammonium bromide were added. The reaction mixture was heated till reflux and kept at reflux, while stirring vigorously. The reaction was monitored with HPLC. After 4 days at reflux, the starting epoxide was completely converted. The mixture was cooled to room temperature. 10 ml of chloroform was added. The organic layer was washed with 3×20 ml of water, dried (Na$_2$SO$_4$), filtrated and evaporated to dryness. Residue: 226 mg (brown oil). Purification of the residue by column chromatography (Merck silica gel 60; eluens: heptane/ethyl acetate=1/1) afforded R-enantiomer of bicalutamide as a white/yellow solid material. Purified yield: 122 mg (43%). HPLC: 96.3% purity. HPLC (chiral column): 94.7% e.e. $^1$H and $^{13}$C NMR in agreement with R-bicalutamide

EXAMPLE 18

N-[4-cyano-3-(trifluoromethyl)phenyl]-4-methyl-2,2-dioxo-1,3,2λ$^6$-dioxathiolane-4-carboxamide (5D)

Reaction Scheme

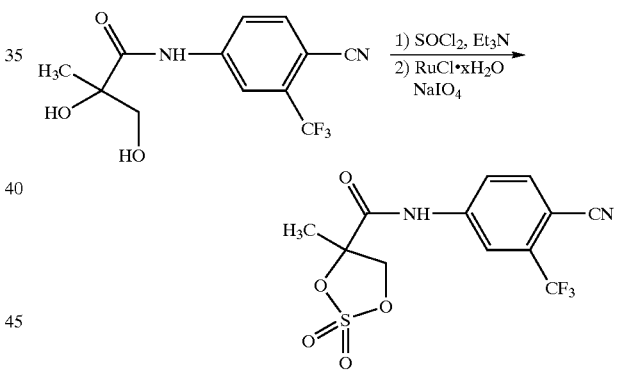

In a 50 ml flask, equipped with a magnetic stirrer, a pre-cooled (0° C.) solution of 0.576 g of the diol (5C) in 10 ml of dichloromethane containing 0.74 ml of triethyl amine was treated dropwise with a solution of 0.2 ml of thionylchloride in 4 ml of dichloromethane over 10 minutes and then set aside for 20 minutes. The mixture was diluted with 50 ml of dichloromethane, washed with 4×25 ml of water, dried (Na$_2$SO$_4$) and concentrated in vacuo. The resultant crude material was dissolved in a mixture of 6.6 ml carbontetrachloride, 6.6 ml of acetonitrile and 6.6 ml of water and treated with 0.535 g of sodium periodate and 3 mg of ruthenium(III) chloride hydrate at room temperature for 1 hour. The reaction mixture was diluted with 50 ml of ethyl acetate and the organic layer was washed with 3×20 ml of water, 2×20 ml of brine, dried (Na$_2$SO$_4$) and concentrated at reduced pressure. The crude product was purified by column chromatography (Merck 60 SiO$_2$, eluens=ethyl acetate/heptane=1/1) to give 0.0.541 g (77%) of a colourless/white syrup. $^1$H-NMR confirmed the structure.

EXAMPLE 19

Methyl 2-methyl-2-oxiranecarboxylate

Reaction Scheme

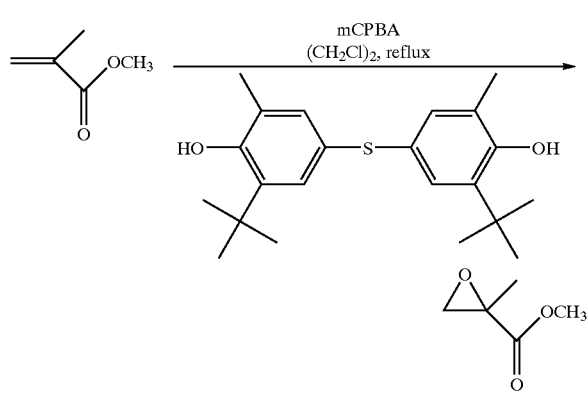

27.5 g of methyl methacrylate, 81.5 g of m-chloroperbenzoic acid and 500 mg of bis(3-tert-butyl-4-hydroxy-5-methyl phenyl) sulfide were refluxed in 550 ml of 1,2-dichloroethane for 48 hours. After cooling (ice), the precipitated m-chlorobenzoic acid was filtered off and the solution was washed with 250 ml of a sodium sulfite solution. The organic layer was washed successively with 250 ml of saturated aqueous $NaHCO_3$, 250 ml of saturated brine and 250 ml of saturated bicarbonate. After drying ($Na_2SO_4$) and evaporation under reduced pressure, 33.61 g of a yellow oil remained. The crude product was distilled under vacuum. A colourless oil was obtained at 30° C. and 5 mbar. Isolated yield: 16.05 g (50.3%). $^1$H-NMR confirmed the expected structure. GC: >99.9% purity

EXAMPLE 20

Methyl 2,3-dihydroxy-2-methylpropionate by Transesterification of Menthol Ester (6C, R=menthyl)

Reaction Scheme

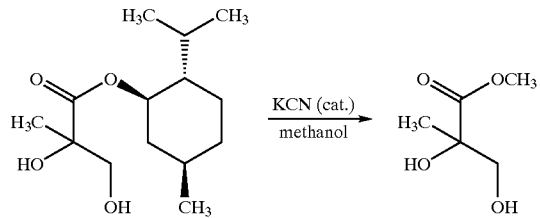

In a 50 ml flask, equipped with a magnetic stirrer, 10 mg of potassium cyanide was added to 0.290 g of menthol ester of 2,3-dihydroxy-2-methylpropionic acid (compound 6C, R=menthyl) in 5 ml of methanol. The reaction mixture was stirred at reflux temperature for 3 days under TLC control (eluens=ethyl acetate/heptane=3/1). The reaction mixture was worked-up by concentration to dryness (clear oil). Purification by column chromatography (Merck 60 $SiO_2$; eluens=heptane/ethyl acetate=1/3) gave 0.080 g (53%) of the title product. $^1$H-NMR confirmed the expected compound.

EXAMPLE 21

Coupling of Methyl 2-methyl-2-oxiranecarboxylate and Sodium-p-fluorobenzenesulfinate Reaction Scheme

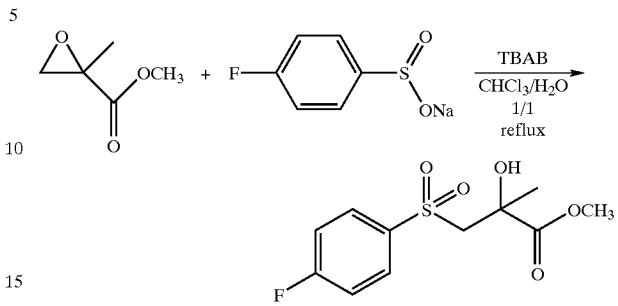

200 mg of the epoxyester of Example 19 was dissolved in a mixture of 15 ml of chloroform and 15 ml of water. 345 mg of sodium-p-fluorobenzenesulfinate and 555 mg of tetrabutylammonium bromide were added. The reaction mixture was heated till reflux and kept at reflux, while stirring vigorously. After 5 days at reflux, TLC showed that the starting epoxide was completely converted. The reaction mixture was cooled to room temperature. 20 ml of chloroform and 20 ml of water were added. The organic layer was washed with 2×30 ml of water, dried ($Na_2SO_4$), filtrated and concentrated at reduced pressure. Purification of the residue by column chromatography (Merck silica gel 60; eluens: ethyl acetate/heptane 1/1) afforded the title compound as a yellow oil. Isolated yield: 146 mg (31%). $^1$H-NMR confirmed the expected structure. GC: 97% purity.

EXAMPLE 22

Separation of Enantiomers of the Diol (5C) by Means of Camphanic Acid Chloride

Step 1: (2S)-3-[4-cyano-3-(trifluoromethyl)anilino]-2-hydroxy-2-methyl-3-oxopropyl 4,7,7-trimethyl-3-oxo-2-oxabicyclo[2.2.1]heptane-1-carboxylate Reaction Scheme

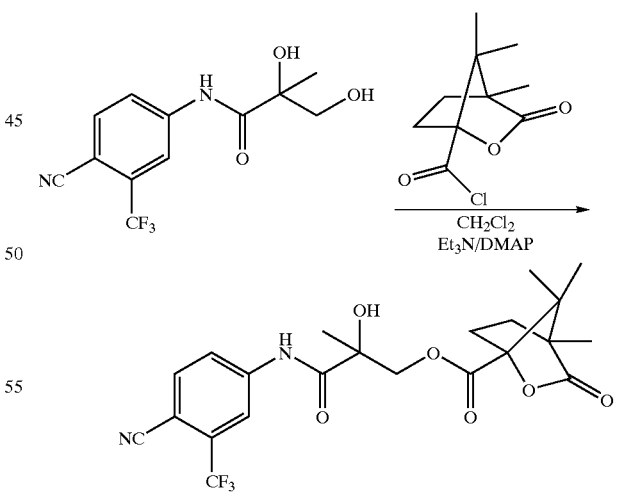

1.8 g of the diol (5C) was dissolved in 150 ml of dichloromethane. 632 mg of triethylamine and 100 mg of dimethylaminopyridine were added. 1.49 g of (−)-camphanic acid chloride was dissolved in 50 ml of dichloromethane. This solution was slowly added via a dropping funnel to the diol solution. 15 minutes after the addition was completed, the reaction mixture was analyzed with HPLC.

The diol was almost completely converted into the camphanic derivative (≈2% of diol left). 50 mg of(−)-camphanic acid chloride and a few drops of triethylamine were added to obtain complete conversion. The reaction mixture was stirred for 15 minutes, transferred into a separation funnel and washed with 200 ml of water, 200 ml of the saturated brine and 200 ml of water. The organic layer was dried (Na$_2$SO$_4$), filtrated and evaporated to dryness under reduced pressure. Residue: 2.81 g (white foam). The obtained diastereoisomers were separated by column chromatography (Merck silica gel 60; eluens: heptane/ethyl acetate 3/1→1/1). One of the isomers (fast moving) was isolated. Isolated yield of single diastereoisomer: 662 mg (white foam). HPLC:>99% d.e. $^1$H-NMR confirmed the expected structure of single S-diastereoisomer.

Step2: (2S)-N-[4-cyano-3-(trifluoromethyl)phenyl]-2,3-dihydroxy-2-methylpropanamide (5C)

Reaction Scheme

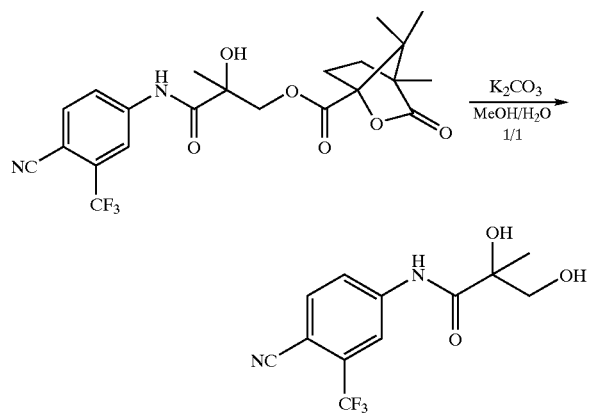

629 mg of the camphane derivative from Step 1 was dissolved in a mixture of 20 ml of methanol and 20 ml of water. 150 mg of potassium carbonate was added. After 30 minutes at room temperature, the conversion was complete according to HPLC. 20 ml water and 20 ml of ethyl acetate were added to the reaction mixture. Layers were separated and the water layer was washed with 2×50 ml of ethyl acetate. The combined organic fractions were washed twice with 100 ml water. The organic phase was dried (Na$_2$SO$_4$), filtrated and evaporated to dryness. Isolated yield: 470 mg (grey solid).

EXAMPLE 23

(2S)-3-[4-cyano-3-(trifluoromethyl)anilino]-2-hydroxy-2-methyl-3-oxopropyl methanesulfonate (5B, L=methanesulfonyloxy)

Reaction Scheme

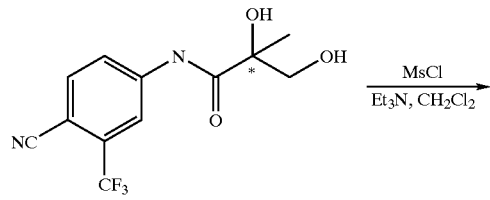

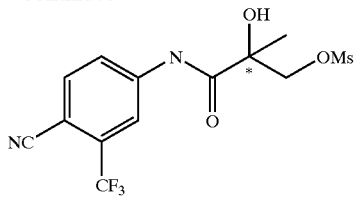

439 mg of chiral diol (5C) of Example 22 was dissolved in 20 ml of dichloromethane. The solution was cooled to 0° C. (ice). 170 mg of triethylamine was added. 174 mg of methanesulfonyl chloride was dissolved in 5 ml of dichloromethane and slowly added to the diol solution. After the addition was completed, the mixture was allowed to warm to room temperature. After 25 minutes at room temperature, the reaction mixture was analyzed with HPLC; there was still 27% of diol present. Next 70 mg of methanesulfonyl chloride was added. After 10 minutes at room temperature, the reaction was completed. 60 ml of ethyl acetate and 60 ml of 0.5 N aqueous HCl were added. The organic layer was washed subsequently with 60 ml of water and 60 ml of saturated NaHCO$_3$, dried (Na$_2$SO$_4$), filtrated and evaporated to dryness. Purification of the residue by column chromatography (Merck silica gel 60; eluens: ethyl acetate) afforded the title compound as a green/black oil. Isolated yield: 473 mg. $^1$H-NMR confirmed the expected structure (2S-enantiomer). HPLC: 94% purity.

The entire disclosure in each of the patents and articles mentioned in the above description is incorporated herein by reference. The invention having been described, it will be readily apparent to those skilled in the art that further changes and modifications in actual implementation of the concepts and embodiments described herein can easily be made or may be learned by practice of the invention, without departing from the spirit and scope of the invention as defined by the following claims.

We claim:

1. A compound of formula (4):

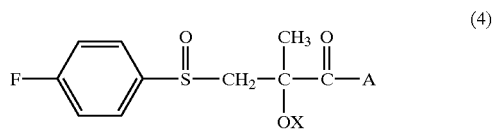

(4)

wherein A represents OR, in which R is a metyhyl, propyl, butyl, pentyl, hexyl, a C$_3$–C$_6$ cycloalkyl, a phenyl, or a benzyl group; X represents hydrogen or X and A join together to form a 5- to 10-membered fused or unfused heterocyclic ring with the proviso that if a ring nitrogen is present, it may be substituted by a 3-trifluoromethyl-4-cyano-phenyl group.

2. The compound according to claim 1, wherein R represents a methyl, propyl, or butyl group.

3. The compound according to claim 2, wherein said propyl group is an iso-propyl group.

4. The compound according to claim 1, wherein R is methyl.

5. The compound according to claim 1, wherein R is a C$_3$–C$_6$ cycloalkyl, a phenyl, or a benzyl group.

6. The compound according to claim 5, wherein R is phenyl.

7. The compound according to claim 1, wherein X and A join together to form a 5- to 10-membered fused or unfused heterocyclic ring with the proviso that if a ring nitrogen is present, it may be substituted by a 3-trifluoromethyl-4-cyano-phenyl group.

8. The compound according to claim 7, wherein said compound is selected from the group consisting of
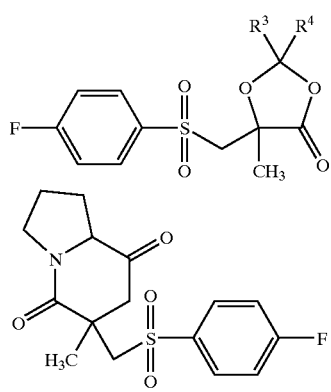
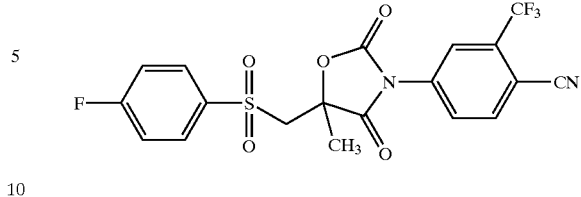
wherein $R^3$ represents a hydrogen, an $C_1$–$C_6$ alkyl or a $C_3$–$C_6$ cycloalkyl and $R^4$ represents a $C_1$–$C_6$ halogenated alkyl.
* * * * *

UNITED STATES PATENT AND TRADEMARK OFFICE
CERTIFICATE OF CORRECTION

PATENT NO. : 6,818,766 B2  Page 1 of 1
APPLICATION NO. : 10/261492
DATED : November 16, 2004
INVENTOR(S) : Thijs et al.

It is certified that error appears in the above-identified patent and that said Letters Patent is hereby corrected as shown below:

In claim 1, line 2, please replace the formula with the following:

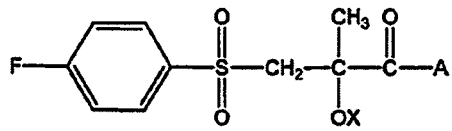

(4)

and in line 3, change "metyhyl" to --methyl--.

Signed and Sealed this

Seventh Day of November, 2006

JON W. DUDAS
*Director of the United States Patent and Trademark Office*